United States Patent [19]

Young

[11] Patent Number: 4,942,254

[45] Date of Patent: * Jul. 17, 1990

[54] METHODS FOR ACID CATALYZED REACTIONS

[75] Inventor: Donald C. Young, Fullerton, Calif.

[73] Assignee: Union Oil Company of California, Brea, Calif.

[*] Notice: The portion of the term of this patent subsequent to May 12, 2004 has been disclaimed.

[21] Appl. No.: 149,735

[22] Filed: Jan. 29, 1988

Related U.S. Application Data

[63] Continuation of Ser. No. 771,259, Aug. 30, 1985, Pat. No. 4,722,986, which is a continuation-in-part of Ser. No. 679,235, Dec. 7, 1984, Pat. No. 4,589,925, and Ser. No. 675,774, Nov. 28, 1984, Pat. No. 4,673,522, and Ser. No. 673,358, Nov. 20, 1984, Pat. No. 4,664,717, and Ser. No. 673,508, Nov. 20, 1984, and Ser. No. 453,496, Dec. 27, 1982, which is a continuation-in-part of Ser. No. 442,296, Nov. 17, 1982, abandoned, and Ser. No. 444,667, Nov. 26, 1982, and Ser. No. 331,001, Dec. 15, 1981, Pat. No. 4,402,852, and Ser. No. 330,904, Dec. 15, 1981, Pat. No. 4,404,116, and Ser. No. 318,629, Nov. 5, 1981, Pat. No. 4,445,925, and Ser. No. 318,368, Nov. 5, 1981, Pat. No. 4,447,253, and Ser. No. 318,343, Nov. 15, 1981, Pat. No. 4,397,675.

[51] Int. Cl.$^5$ .................. C07C 101/02; C07C 149/40; C08F 8/12; C08F 8/34

[52] U.S. Cl. .................................... 558/250; 560/155; 560/152; 560/234; 562/426; 562/507; 562/512

[58] Field of Search ....................... 560/155, 152, 234; 558/230, 250; 562/426, 507, 512

[56] References Cited

U.S. PATENT DOCUMENTS

| Re. 1,995 | 6/1965 | Hoffman | 127/36 |
|---|---|---|---|
| 1,340,708 | 5/1920 | Fjellanger | 71/28 |
| 1,878,852 | 9/1932 | Hoppler | 127/36 |
| 1,917,539 | 7/1933 | Miles | 127/37 |
| 1,919,623 | 7/1933 | Dreyfus | 127/37 |
| 2,237,459 | 4/1941 | Thompson | 502/216 |
| 2,468,725 | 4/1949 | Gresham et al. | 560/152 |
| 2,767,108 | 10/1956 | Fetzer | 127/34 |
| 2,978,359 | 4/1961 | Wedell | 427/389 |
| 3,098,093 | 7/1963 | Hogemeyer Jr. et al. | 560/234 |
| 3,432,482 | 3/1969 | Ohfuka et al. | 526/220 |
| 3,558,530 | 1/1971 | Schroeder et al. | 521/94 |
| 3,660,070 | 5/1972 | Maruta et al. | 71/64.07 |
| 3,778,431 | 12/1973 | Knightlinger | 536/47 |
| 3,816,375 | 6/1974 | Bozer et al. | 528/243 |
| 3,873,734 | 3/1975 | Higgins et el. | 426/69 |
| 3,878,304 | 4/1975 | Moore | 426/69 |
| 3,918,952 | 11/1975 | Neumiller | 71/29 |
| 4,116,664 | 9/1970 | Jones | 71/29 |
| 4,214,888 | 7/1980 | Young | 71/28 |
| 4,310,343 | 1/1982 | Verdegaal et al. | 71/28 |
| 4,315,763 | 2/1982 | Stoller et al. | 71/29 |
| 4,397,675 | 8/1983 | Young | 71/28 |
| 4,402,852 | 9/1983 | Young | 71/28 |
| 4,404,116 | 9/1983 | Young | 71/28 |
| 4,439,348 | 3/1984 | Akerberg | 502/167 |
| 4,445,925 | 5/1984 | Young | 71/28 |
| 4,447,253 | 5/1984 | Young | 71/28 |
| 4,451,577 | 5/1984 | Coss | 502/167 |
| 4,474,925 | 10/1984 | Sartoretto et al. | 524/598 |
| 4,512,813 | 4/1985 | Young | 134/27 |
| 4,522,644 | 6/1985 | Young | 71/28 |
| 4,589,925 | 5/1986 | Young | 134/3 |
| 4,626,417 | 12/1986 | Young | 423/235 |
| 4,664,717 | 5/1987 | Young | 134/27 |
| 4,673,522 | 6/1987 | Young | 252/87 |
| 4,686,017 | 8/1987 | Young | 423/235 |
| 4,722,986 | 2/1988 | Young | 527/203 |
| 4,755,265 | 7/1988 | Young | 294/451 |

OTHER PUBLICATIONS

Chemical Abstracts, vol. 93, entry 25920h Ge. 2,833,512.
"The Chemistry of Carboxylic Acids and Esters", Interscience Publishers, 1969, pp. 732–759.
Donald C. Young, U.S. Ser. No. 07/009,829 filed Feb. 2, 1987, Polysaccharide Compositions.
Donald C. Young, U.S. Ser. No. 06/453,496 filed Dec. 27, 1982 for Acid Catalyzed Reaction and Compositions for use Therein.

(List continued on next page.)

*Primary Examiner*—Joseph L. Schofer
*Assistant Examiner*—Peter F. Kulkosky

[57] ABSTRACT

Compositions containing sulfuric acid and one or more of certain chalcogen-containing compounds in which the chalcogen compound/$H_2SO_4$ molar ratio is below 2 contain the mono-adduct of sulfuric acid which is catalytically active for promoting organic chemical reactions. Suitable chalcogen-containing compounds have the empirical formula.

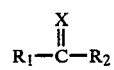

wherein X is a chalcogen, each of $R_1$ and $R_2$ is independently selected from hydrogen, $NR_3R_4$, and $NR_5$, at least one of $R_1$ and $R_2$ is other than hydrogen, each of $R_3$ and $R_4$ is hydrogen or a monovalent organic radical, and $R_5$ is a divalent organic radical. Such compositions are useful for catalyzing organic reactions such as oxidation, oxidative addition, reduction, reductive addition, esterification, transesterification, hydrogenation, isomerication (including racemization of optical isomers), alkylation, polymerization, demetallization of organometallics, nitration, Friedel-Crafts reactions, and hydrolysis. Novel catalysts are disclosed which involve combinations of the chalcogen compound-sulfuric compositions with one or more transition metal halides and/or with one or more surfactants. The surfactant-containing compositions are particularly useful for the treatment of materials containing lipophilic substances. Novel compositions containing a chalcogen compound-sulfuric acid component and one or more organic reactants are also disclosed.

9 Claims, No Drawings

OTHER PUBLICATIONS

Donald C. Young, U.S. Ser. No. 06.455,268 filed Jan. 3, 1983 for Cellulosic Compositions & Meths. F/Treating Cellulosic Materials.
Donald C. Young, U.S. Ser. No. 06/455,317 filed Jan. 3, 1983, for Plant Seed Compositions and Methods for Treating Plant Seeds.
Donald C. Young, U.S. Ser. No. 06/673,508 filed Nov. 20, 1984 for Thermally Stable Urea-Sulfuric Acid Compositions and Methods of Manufacture.
Donald C. Young, U.S. Ser. No. 06/688,689 filed Jan. 3, 1983 for Pesticidal Compositions and Methods for Controlling Pests.
Donald C. Young, U.S. Ser. No. 06/783,368 filed Oct. 3, 1985 for Herbicidal Compositions.
Donald C. Young, U.S. Ser. No. 06/822,285 filed Jan. 24, 1986 for Methods for Chemiclly Reducing Nitrogen Oxides.
Donald C. Young, U.S. Ser. No. 06/918,546 filed Oct. 10, 1986 for Methods for Facilitating the Harvest of Food Crops.
Donald C. Young, U.S. Ser. No. 07/021,200 filed Mar. 3, 1987 for Electrolytic Cell.
Donald C. Young, U.S. Ser. No. 07/050,530 filed May 13, 1987 for Methods for Removing Obstructions From Conduits.
Donald C. Young, U.S. Ser. No. 07/116,472 filed Nov. 3, 1987 for Systemic Herbicides and Methods of Use.
Donald C. Young, U.S. Ser. No. 07/149,424 filed Jan. 29, 1988 for Acid Catalyzed Reduction.
Donald C. Young, U.S. Ser. No. 07/149,431 filed Jan. 29, 1988 for Friedel-Crafts Reactions.
Donald C. Young, U.S. Ser. No. 07/149,701 filed Jan. 29, 1988 for Acid-Catalyzed Nitration.
Sulfur Institute Bulletin No. 10 (1964), "Adding Plant Nutrient Sulfur to Fertilizer".
Kirk-Othmer Encyclopedia of Chemical Technology, Third Edition, John Wiley and Sons, New York, 1980, vol. 5, pp. 31-33 and 55-61; vol. 9, pp. 291-374; vol. 11, pp. 295-300, 662-665 and 694-695; and vol. 12, pp. 852-857 and 867-869.
"Organic Chemistry of Bivalent Sulfur", Chemical Publishing Co., 1962, pp. 14, 15, 94 and 95.
Donald C. Young, U.S. Ser. No. 07/149,734 filed Jan. 29, 1988 for Alkylation.
Donald C. Young, U.S. Ser. No. 07/150,026 filed Jan. 29, 1988 for Isomerization.
Donald C. Young, U.S. Ser. No. 07/149,702 filed Jan. 29, 1988 for Acid Catalysts and Methods of Use.
Donald C. Young, U.S. Ser. No. 07/150,076 filed Jan. 29, 1988 for Acid-Catalyzed Oxidative Reactions.
Donald C. Young, U.S. Ser. No. 07/150,077 filed Jan 29, 1988 for Demetallizing Organometallic Compounds.
Donald C. Young, U.S. Ser. No. 07/150,079 filed Jan. 29, 1988 for Acid-Catalyzed Polymerization.
Donald C. Young, U.S. Ser. No. 07/150,224 filed Jan. 29, 1988 for Isomerization.
Donald C. Young, U.S. Ser. No. 07/150,230 filed Jan. 29, 1988 for Acid-Catalyzed Reactions.
Donald C. Young, U.S. Ser. No. 07/235/005 filed Aug. 22, 1988 for Vegetation Control.
Donald C. Young, U.S. Ser. No. 07/235,799 filed Aug. 22, 1988 for Methods for Controlling Vegetation.
Donald C. Young, U.S. Ser. No. 07/236,344 filed Aug. 22, 1988 for Systemic Herbicidal Compositions and Methods of Use.
Science News, vol. 123, No. 23, Jun. 4, 1983, p. 366, Science Service, Inc. 1719 N Street, N.W., Washington, D. C. "Cellulose Digestion" by Lab Bacteria.
The Condensed Chemical Dictionary, Seventh Edition, Van Nostrand Reinhold Co., New York, 1969, p. 908.
D. F. duToit, Verslag Akad. Wetenschappen, 22 5/3-4 (abstracted in Chemical Abstracts, 8, 2346, (1914)).
L. H. Dalman, "Ternary Systems of Ures and Acids". I. Urea, Nitric Acid and Water. II. Ures, Sulfuric Acid and Water. III. Urea, Oxalic Acid and Water; Jacs 56, 549-553 (1934).

METHODS FOR ACID CATALYZED REACTIONS

RELATED APPLICATIONS

This application is a continuation of my co-pending application Ser. No. 771,259, ACID CATALYSTS AND METHODS OF USE, filed Aug. 30, 1985, now U.S. Pat. No. 4,722,986 which was a continuation-in-part of my copending applications Ser. No. 679,235, METHODS FOR CLEANING MATERIALS, filed Dec. 7, 1984, now U.S. Pat. No. 4,589,925; Ser. No. 675,774, METHODS FOR REMOVING OBSTRUCTIONS FROM CONDUITS, filed Nov. 28, 1984, now U.S. Pat. No. 4,673,522; Ser. No. 673,358, METHODS FOR HYDROLYZING POLYSACCAHARIDES AND COMPOSITIONS USEFUL THEREIN, filed Nov. 20, 1984, now U.S. Pat. No. 4,664,717; Ser. No. 673,508, THERMALLY STABLE UREA-SULFURIC ACID COMPONENTS AND METHODS OF MANUFACTURE, filed Nov. 20, 1984; and Ser. No. 453,496, ACID-CATALYZED REACTIONS AND COMPOSITIONS FOR USE THEREIN, filed Dec. 27, 1982, the last of which was a continuation in part of Ser. No. 442,296, SYSTEMIC HERBIDICAL COMPOSITION AND METHODS OF USE, filed Nov. 17, 1982, now abandoned; Ser. No. 444,667, METHODS FOR CONTROLLING VEGETATION, filed Nov. 26, 1982, now abandoned; Ser. No. 331,001, NONCORROSIVE UREA-SULFURIC ACID COMPOSITIONS, filed Dec. 15, 1981, now U.S. Pat. No. 4,402,852; Ser. No. 330,904, NONCORROSIVE UREA-SULFURIC ACID REACTION PRODUCTS, filed Dec. 15, 1981, now U.S. Pat. No. 4,404,116; Ser. No. 318,629, METHOD OF PRODUCING CONCENTRATED UREA-SULFURIC ACID REACTION PRODUCTS, filed Nov. 5, 1981, now U.S. Pat. No. 4,445,925; Ser. No. 318,368, TOPICAL FERTILIZATION METHODS AND COMPOSITIONS FOR USE THEREIN, filed Nov. 5, 1981, now U.S. Pat. No. 4,447,253; and Ser. No. 318,343, METHOD FOR PRODUCING UREA-SULFURIC ACID REACTION PRODUCTS, filed Nov. 5, 1981, now U.S. Pat. No. 4,397,675.

BACKGROUND OF THE INVENTION

1. Field of the Invention

This invention relates to the field of acid-catalyzed organic reactions and particularly to methods of conducting acid-catalyzed reactions of organic compounds which reactions are promoted by strong acids. The invention also relates to novel acidic compositions useful in such reactions.

2. Description of the Art

The ability of sulfuric acid to catalyze a variety of organic reactions is well known. It is also known that urea (a chalcogen compound useful in this invention) and sulfuric acid will combine to form adducts including the monourea-sulfuric acid adduct and the diurea-sulfuric acid adduct. For instance, D. F. du Toit, Verslag Akad. Wetenschappen, 22, 573–4 (abstracted in Chemical Abstracts, 8, 2346, 1914) disclosed that urea forms certain compounds with oxalic, acetic hydrochloric, nitric and sulfuric acids. L. H. Dalman, "Ternary Systems of Urea and Acid. I. Urea, Nitric Acid and Water. II. Urea, Sulfuric Acid and Water. III. Urea, Oxalic Acid and Water"; JACS, 56, 549–53 (1934), disclosed the phase relationships between the solid phase and saturated solutions containing urea and sulfuric acid at 10° C. and 25° C. The Sulfur Institute, Sulfur Institute Bulletin No. 10 (1964), "Adding Plant Nutrient Sulfur to Fertilizer", disclosed that urea reacts with sulfuric acid to form two complexes of "urea sulfate" which are useful fertilizers. Methods of manufacturing certain combinations of urea and sulfuric acid are disclosed by Verdegaal et al. in U.S. Pat. No. 4,310,343 and by Jones in U.S. Pat. No. 4,116,664.

A wide variety of organic conversions are catalyzed by the proton-donating ability of strong acids. Such reactions have been extensively investigated and have been widely discussed in the literature. For instance, the Kirk-Othmer Encyclopedia of Chemical Technology, Third Edition, John Wiley and Sons, New York, 1980, discusses a variety of organic reactions that are catalyzed by strong acids including mineral acids, transition metal halides such as Friedel-Crafts catalysts, conjugate Friedel-Crafts catalysts, and others. Kirk-Othmer defines acid-catalyzed reactions as those in which a proton is transferred from the catalyst to the reactant which is thereby converted to an unstable state which immediately leads to the reaction under consideration. (Volume 5, page 33). While the proton donation mechanism of acid-catalyzed reactions referred to in Kirk-Othmer may or may not account for the reactions that take place in all acid-catalyzed reactions, it is known that strong acids promote numerous reactions including oxidative addition, reductive addition, esterification, transesterification, hydrogenation, isomerization (including racemization of optical isomers), hydrolysis and alcoholisis, alkylation, olefin polymerization, Friedel-Crafts reactions, demetalization of organics, and nitration reactions, among others. Strong acids known to be capable of promoting such acid-catalyzed organic reactions include sulfuric acid, nitric acid, hydrochloric acid, transition metal halides including the so-called Friedel-Crafts catalysts, for example, the halides of aluminum, gallium, boron, titanium, vanadium, tin and others, and conjugate Friedel-Crafts catalysts also known as Bronsted-Lewis superacid mixtures (Kirk-Othmer, V. 11, 295) such as mineral acid adducts of transition metal halides.

All of the known strong acid catalysts, and the methods involving their use for the promotion of acid-catalyzed organic reactions, suffer from one or more disadvantages. For instance, the strong mineral acids promote side reactions which form undesired by-products, destroy the organic feed material or product, and/or consume or deactivate the catalyst. Sulfuric acid is a strong sulfating, sulfonating, oxidizing, and dehydrating agent, and by virtue of those activities, it is consumed in most organic reactions by side reactions involving these mechanisms. Furthermore, the sulfonating and oxidizing activities of sulfuric acid result in the sulfonation and oxidation of organic feedstocks and/or products. Similar deficiencies exist with the other strong mineral acids such as hydrochloric and nitric acids. Hydrochloric acid chlorinates the reactants and thereby consumes the feed to produce unwanted chlorinated by-products. Nitric acid oxidizes and/or nitrates organic compounds. Hydrofluoric acid fluorinates organic reactants and products. The transition metal halides, including the Friedel-Crafts catalysts, are difficult to handle in that they must be isolated from water and reducing agents. Such catalysts also halogenate organic feedstocks and products.

Accordingly, a need exists for improved methods of conducting acid-catalyzed organic reactions and for improved acid catalysts for use in such reactions which will promote the desired acid-catalyzed organic reaction yet reduce or eliminate the side reactions normally associated with acid-catalyzed organic reactions.

It is therefore a principal object of this invention to provide novel methods for the acid-catalyzed conversion of organic compounds.

Another object is the provision of novel methods for conducting acid-catalyzed reactions of organic compounds in the presence of compositions which comprise sulfuric acid.

Another object of this invention is the provision of novel acid catalysts comprising sulfuric acid which are effective for conducting acid-catalyzed organic reactions.

Another object of this invention is the provision of novel compositions which are useful for conducting acid-catalyzed organic reactions.

Another object of this invention is the provision of novel catalysts comprising sulfuric acid which have improved activity in the presence of lipophilic materials.

Yet another objective of this invention is the provision of novel methods for catalyzing organic reactions with sulfuric acid.

Another object is the provision of novel methods for the oxidative addition of organic compounds.

Yet another object is the provision of novel methods for reductive addition of organic compounds.

Another object is the provision of novel sulfuric acid-containing compositions useful for conducting organic reactions.

Another object is the provision of novel methods for the esterification and transesterification of organic compounds.

Yet another object of this invention is the provision of novel methods for hydrogenating organic compounds containing olefinic unsaturation.

Another object is the provision of novel methods for isomerizing organic compounds.

Yet another object is the provision of novel methods for the hydrolysis, alcoholisis, thiolosis, and amination of organic compounds.

Another object is the provision of novel methods for the alkylation of organic compounds.

Yet another object is the provision of novel methods for polymerizing olefinic compounds.

Yet another object is the provision of novel conjugate Friedel-Crafts catalysts.

Another object is the provision of novel Friedel-Crafts catalyzed organic reactions.

Yet another object of this invention is the provision of novel methods for demetalizing organic compounds.

Another object is the provision of novel methods for nitrating organic compounds.

Other objects, aspects and advantages of this invention will be apparent to one skilled in the art in view of the following disclosure and the appended claims.

SUMMARY OF THE INVENTION

Briefly, the invention provides novel (1) surfactant-containing catalyst compositions suitable for promoting acid-catalyzed organic reactions, (2) conjugate Friedel-Crafts acid catalysts suitable for promoting acid-catalyzed organic reactions, (3) reactant-containing compositions containing a chalcogen-containing compound, sulfuric acid, and one or more reactants useful for conducting organic reactions, and (4) methods of conducting acid-catalyzed organic reactions.

It has been discovered that compositions which contain one or more of certain chalcogen-containing compounds and sulfuric acid and in which the molar ratio of chalcogen compound to sulfuric acid is less than 2 are highly useful as catalysts, particularly for organic reactions. Within this range of molar ratios, at least a portion of the sulfuric acid will be in the form of the mono adduct of sulfuric acid, which adduct is the active acid catalyst useful herein. The useful chalcogen-containing compounds have the empirical formula

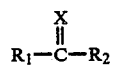

wherein X is a chalcogen, each of $R_1$ and $R_2$ is hydrogen, $NR_3R_4$ or $NR_5$, at least one of $R_1$ and $R_2$ being other than hydrogen, each of $R_3$ and $R_4$ is hydrogen or a monovalent organic radical, and $R_5$ is a divalent organic radical.

Among the novel catalysts of the present invention are compositions containing the chalcogen compound-sulfuric acid component in combination with a surfactant and/or solvent. Such catalysts are especially useful for promoting chemical reactions involving relatively lipophilic organic materials, since surfactants and/or solvents accentuate the activity of the chalcogen compound-acid component toward such materials.

Also provided in the invention are conjugate Friedel-Crafts catalysts containing combinations of the chalcogen compound-sulfuric acid component described above, with or without surfactant, and one or more transition metal halides.

Novel reactant-containing compositions are also provided containing the described chalcogen compound-sulfuric acid component, with or without a surfactant, and one or more reactants which are useful in conducting organic reactions.

The novel methods of this invention involve acid-catalyzed reactions of one or more organic compounds in the presence of the described catalysts. The solvent and/or surfactant-containing catalysts are particularly useful for many acid-catalyzed organic reactions, particularly those in which the more lipophilic, i.e., hydrophobic materials are present. It has been found that surfactants and solvents accentuate the activity of the chalcogen-acid component toward more lipophilic substrates. Similarly, the novel conjugate acid catalysts can be employed in the novel methods of this invention.

In particular, the novel methods of this invention involve the conversion of organic materials, at least in part, by the acid-catalytic activity of sulfuric acid. Thus, they include all acid-catalyzed organic reactions that are catalyzed by sulfuric acid, such as (a) oxidation of one or more organic compounds in the presence of an oxidant;

(b) reduction of one or more organic compounds by reaction with a reducing agent such as hydrogen;

(c) hydrolysis of one or more organic compounds by reaction with water and/or one or more alcohols and/or thiols;

(d) oxidative addition of one or more organic compounds by reaction with an oxidant;

(e) reductive addition of organic compounds by reaction with a reducing agent;

(f) esterification of amides, nitriles, carboxylic acids, acyl halides, thiocarboxylic acids, and/or carboxylic acid anhydrides by reaction with alcohols and/or thiols;

(g) hydrogenation of organic compounds containing carbon-to-carbon unsaturation by reaction with hydrogen;

(h) alkylation of organic compounds by reaction with an organic alkylating agent having at least one carbon-to-carbon olefinic bond;

(i) polymerization of organic compounds containing olefinic unsaturation in the presence of an oxidant;

(j) Friedel-Crafts reactions of organic compounds with hydrocarbyl halides;

(k) isomerization of hydrocarbons having four to about twenty carbon atoms per molecule;

(l) demetalization or organo-metal compounds by reaction with water and/or alcohols; and (m) nitration of organic compounds by reaction with a nitrating agent such as nitric oxide.

The methods and compositions of this invention eliminate most, if not all, of the deficiencies associated with the acid-catalyzed conversion of organic compounds in the presence of sulfuric acid. The chalcogen compound-sulfuric acid components minimize or completely eliminate the undesirable oxidizing, dehydrating and sulfonating activity of sulfuric acid yet retain the acid's strong proton donating ability. Thus, the sulfuric acid contained in the chalcogen compound-acid component is not destroyed during acid-catalyzed organic reactions due to sulfonation, oxidation or other reactions associated with sulfuric acid. At the same time, organic feed materials are not destroyed or converted to undesirable by-products by the side reactions usually associated with sulfuric acid. All of these benefits exist with all forms of chalcogen compound-sulfuric acid components employed in the methods of this invention, including the novel surfactant-containing catalysts and the novel conjugate transition metal halide catalysts. Moreover, the solvent and surfactant-containing catalysts exhibit improved catalytic activity for the conversion of organic compounds in accordance with the methods of this invention, particularly for the conversion of more lipophilic compounds and of organic materials which contain lipophilic matter, such as fats, waxes, and higher molecular weight organic substances.

Without intending to be constrained to any particular theory, it is presently believed that adducting sulfuric acid with compounds, such as the described chalcogen compounds, capable of donating electrons to the sulfuric acid modifies the lability of the acid hydrogens in a manner which inhibits the acid's propensity for undesired side reactions. Stronger electron donors are believed to inhibit acid hydrogen liability to a greater extent as does the addition of two, rather than one, chalcogen molecules to each acid molecule. For instance, the monourea adduct of sulfuric acid is a selective, active acid catalyst while the diurea adduct is essentially inactive as an acid catalyst.

DETAILED DESCRIPTION OF THE INVENTION

This invention provides novel (1) surfactant-containing chalcogen compound-sulfuric acid combinations which are effective acid catalysts for promoting organic conversions, (2) conjugate Friedel-Crafts catalysts which comprise combinations of transition metal halides and the described chalcogen compound-acid components, (3) compositions containing the described novel catalysts of this invention, with or without surfactant, and one or more reactants, which reactants are useful in conducting organic reactions, and (4) methods of conducting acid-catalyzed organic reactions, particularly organic reactions known to be catalyzed by sulfuric acid.

The chalcogen compound-sulfuric acid components useful in the methods of this invention contain a combination of sulfuric acid and one or more of certain chalcogen compounds in which the molar ratio of the chalcogen compound to sulfuric acid is below 2. Within this range of molar ratios, at least a portion of the sulfuric acid is present as the mono-adduct of sulfuric acid. In one embodiment, the chalcogen compound-acid component may optionally contain a surfactant, solvent or other components. Surfactants and solvents increase the activity of the acid component toward organic materials, particularly toward organic materials that contain lipophilic constituents such as fats, oils, waxes and the like. The chalcogen compound-sulfuric acid component, with or without surfactant, may also be combined with one or more organic or inorganic reactants which participate in the desired organic reaction to form a composition useful in conducting the desired organic reaction. In another embodiment, the chalcogen-acid component, with or without surfactants, can be combined with a conventional transition metal halide catalyst to form a conjugate Friedel-Crafts catalyst useful in these methods.

The methods of this invention involve the acid-catalyzed conversion of organic compounds. In particular, these methods can be employed for the acid-catalyzed conversion of any organic material that can be converted by sulfuric acid catalysis, and usually without the occurrence of undesirable side reactions normally associated with sulfuric acid. Illustrative of suitable acid-catalyzed reactions are oxidation, particularly oxidative addition; esterification; transesterification; hydrogenation, isomerization, including racemization of optical isomers; hydrolysis and alcoholisis by reaction with water, alcohols, or thiols; alkylation; olefin polymerization; Friedel-Crafts reactions; demetalization; and nitration. In accordance with these methods, the organic reactant (or reactants) is contacted with the chalcogen compound-sulfuric acid component in the form of a solution in water or other solvents, or as a molten mixture of chalcogen compound and sulfuric acid.

The chalcogen compound-sulfuric acid components are reaction products of sulfuric acid and one or more of certain chalcogen-containing compounds in which the molar ratio of chalcogen compound to sulfuric acid is below 2. In such components, at least a portion of the sulfuric acid is present as the mono-adduct of sulfuric acid and the chalcogen compound. These components may be employed in the methods disclosed herein, as melts, as solutions of such mixtures in water or other solvents, or as solids in which the chalcogen compound-sulfuric acid component is impregnated or exchanged into a solid support such as carbon, refractory oxides such as silica, alumina, and the like, acid or basic ion exchange resins or zeolites such as the natural and synthetic aluminosilicates, and combinations of such supports. The catalysts may also contain optional components such as surfactants and transition metal halides. Other components that do not substantially negate the proton-donating activity of the monoadduct of sulfuric acid may also be present.

The useful chalcogen-containing compounds have the empirical formula

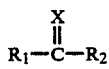

wherein X is a chalcogen, $R_1$ and $R_2$ are independently chosen from hydrogen, $NR_3R_4$ or $NR_5$, with at least one of $R_1$ and $R_2$ being other than hydrogen, $R_3$ and $R_4$ are independently chosen from hydrogen or a monovalent organic radical, and $R_5$ is a divalent organic radical. One of the monovalent radicals $R_3$ and $R_4$ can be hydrogen, and either or both of $R_3$ and $R_4$ can be any organic radical including alkyl, aryl, alkenyl, alkenylaryl, aralkyl, aralkenyl, cycloakyl, cycloalkenyl, or alkynyl, which can be unsubstituted or substituted with pendant functional groups such as hydroxyl, carboxyl, oxide, thio, thiol, or others, and they can contain acyclic or cyclic heteroatoms such as oxygen, sulfur, nitrogen, or others. $R_5$ can be any dialent organic radical such as alkdyl, ardyl, alkenydyl, alkyndyl, aralkdyl, aralkendyl, which may contain pendant atoms or substituents and/or acyclic or cyclic heteroatoms as described for $R_3$ and $R_4$. Preferably, both $R_1$ and $R_2$ are other than hydrogen, both $R_3$ and $R_4$ are selected from hydrogen or hydrocarbyl radicals which, in combination, contain about 10 carbon atoms or less, and X is preferably oxygen or sulur, most preferably oxygen. Such substituents are presently preferred due to their relatively higher chemical stability. Particularly preferred chalcogen-containing compounds are urea, thiourea, formamide, and combinations of these.

The chalcogens are elements of Periodic Group VI-B and include oxygen, sulfur, selenium, tellurium, and polonium. Oxygen and sulfur are presently preferred due to low cost, availability, low toxicity and chemical activity, and oxygen is the most preferred.

The chalcogen compound-sulfuric acid components may contain unreacted (free) sulfuric acid or the di-adduct of sulfuric acid. Useful and preferred proportions of chalcogen compound, sulfuric acid, and of the mono- and di-adducts of sulfuric acid, relative to each other, can be conveniently expressed in terms of the chalcogen compound/sulfuric acid molar ratio. This ratio will be below 2, usually within the range of about ¼ to about 7/4, preferably about ½ to about 3/2, and most preferably between about 1/1 and about 3/2. Molar ratios within the range of about ¼ to about 7/4 define compositions in which at least 25 percent of the sulfuric acid is present as the mono-adduct of sulfuric acid. Molar ratios within the range of ½ to about 3/2 define compositions in which at least 50 percent of the sulfuric acid is present as the mono-adduct. The most preferred molar ratio range of about 1/1 to about 3/2 defines compositions which contain essentially no uncomplexed sulfuric acid and in which at least 50 percent of the sulfuric acid is present as the mono-adduct of sulfuric acid. The most preferred combinations have chalcogen compound/sulfuric acid molar ratios of about 1/1. In such compositions essentially all of the sulfuric acid is present as the mono-adduct of sulfuric acid, and such compositions are essentially free of uncomplexed sulfuric acid. Substantial amounts of uncomplexed sulfuric acid, i.e., sulfuric acid that is not complexed with a chalcogen compound as either the mono- or di-adduct, are less preferred since sulfuric acid, when present in substantial amounts, may promote side reactions such as oxidation, sulfonation, dehydration and/or other reactions. While the di-adduct is generally not detrimental to the performance of the mono-adduct components as acid catalysts for organic reactions, it has little or no proton-donating ability and thus little or no activity as a catalyst for acid-catalyzed organic reactions.

Useful solutions contain a catalytically active amount of the mono-adduct of sulfuric acid in a suitable solvent. Very low mono-adduct concentrations, e.g., on the order of about 0.5 weight percent of the solution (or melt), are sufficient to promote a variety of acid-catalyzed organic reactions. However, higher concentrations of the mono-adduct are generally preferred. Thus, the solutions will usually contain at least 0.5, generally at least about 1, preferably at least about 5, and most preferably at least about 10 weight percent chalcogen compound and sulfuric acid based on the combined weight of those two components. Higher concentrations of chalcogen compound and sulfuric acid provide increased catalytic activity. For instance, solutions containing at least 50 percent, and even 85 weight percent or more of the combination of chalcogen compound and sulfuric acid, in combination, will usually constitute 0.5 to about 90, normally about 1 to about 90, and preferably about 5 to about 90 weight percent of the solution.

Any solvent suitable for dissolving the chalcogen compound-sulfuric acid component under the reaction conditions can be employed. Suitable solvents include polar solvents such as water, dimethylsulfoxide (DMSO), halogenated hydrocarbons such as trichloromethane, oxygenated hydrocarbons such as methylethylketone and tetrahydrofuran, and the like. The solvent is preferably not reactive with the chalcogen compound-sulfuric acid component, the organic feed, intermediates or products, or other components employed in the acid-catalyzed organic reactions unless, or course, the organic feed is also employed as the solvent for the urea-sulfuric acid component.

When water is employed as the only solvent, or as a component of the solvent, I have observed that, at relatively high water concentrations, water begins to displace the chalcogen compound as an adduct on the sulfuric acid thereby, in a manner of speaking, releasing free sulfuric acid into the system. This process is reversible; i.e., as water is removed from the system the chalcogen compound-sulfuric acid adduct reforms. For these reasons, the presently preferred compositions and catalyst systems have $H_2O$/(chalcogen compound $+H_2SO_4$) molar ratios of about 5 or less, most preferably about 2.5 or less.

Melts of the chalcogen compound-sulfuric acid component-containing compositions that have melting points above ambient temperature, e.g., about 70° F., can also be employed to catalyze the acid-catalyzed organic reactions. The active components useful in this embodiment are solids at ambient temperature and are converted to melts by heating them to elevated reaction temperatures. Within this embodiment, the melts will usually contain at least about 50, and preferably at least about 80 weight percent of the chalcogen compound-sulfuric acid component based on the combined weight of chalcogen compound and sulfuric acid. The melts will usually contain at least about 20, generally at least about 50, preferably at least about 80, weight percent of the preferred mono-adduct of sulfuric acid.

The compositions employed in the methods of this invention may also contain one or more surfactants which are preferably, although not necessarily, chemically stable for a significant period of time in the presence of the acid adduct component and in the presence of other components employed in the methods of this invention. Surfactants increase the activity of the acid adduct toward essentially all non-polar organic compounds including lipophilic organic materials such as waxes, proteins, ligands, fats, alkanes, high molecular weight acids, alcohols, and the like. For instance, surfactants enhance the activity of the liquid acid adduct compositions toward cellulosic material such as growing or harvested vegetation which is coated with or which contains a significant amount of waxy cuticle. Thus, surfactants enhance the acid-catalyzed hydrolysis of lipid-containing cellulosic materials and increase the herbicidal activity of the urea-sulfuric acid component toward growing vegetation as discussed hereinafter and in my copending application Ser. No. 444,667 referred to above and incorporated herein by reference in its entirety. The herbicidal activity of the described chalcogen compound-sulfuric acid components is apparently due, at least in part, to their ability to catalyze the chemical conversion of cellulose and/or other organic compounds in plant matter. As described herein, these chalcogen compound-sulfuric acid components are capable of catalyzing reactions involving organic compounds other than plant matter, as well.

The selected surfactant is preferably sufficiently chemically stable in the liquid or solid compositions, or in the melts formed from the solid compositions, to assure that the surfactant retains sufficient wetting ability toward the organic material to be converted, for a period of time required to manufacture, store, transport and employ the chalcogen compound-sulfuric acid component. The stability of any surfactant can be readily determined by adding an amount of the surfactant to the chalcogen compound-sulfuric acid composition in which it is to be employed and monitoring the combination by conventional nuclear magnetic resonance (NMR) analytical techniques. NMR can be used to monitor the frequency and magnitude of spectral peaks characteristic of a selected nucleus, e.g., a hydrogen nucleus in the surfactant. Persistent spectral peak magnitude and frequency over a period of 5 to 6 hours indicate stability. Diminished peak magnitude, or a shift in peak frequency associated with the selected nucleus, indicates instability, i.e., that the arrangement of functional groups in the surfactant molecule has been modified.

Illustrative of classes of stable surfactants are nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

The surfactant concentration is preferably sufficient to increase the wetting ability of the chalcogen compound-acid component for the organic material to be converted. Even very minor surfactant concentrations increase the wetting ability of the acid-adduct component to some extent. Surfactant concentration will usually be at least about 0.05, generally at least about 0.1, and preferably at least about 0.2 weight percent of the solution as it is employed in the methods of this invention. Surfactant concentrations of about 0.2 to about 1 weight percent are adequate in most applications.

The chalcogen compound-sulfuric acid component can be combined with transition metal halides to form the conjugate acid of the acid adduct with the transition metal halide. Such conjugate acids of transition metal halides, such as Friedel-Crafts catalysts and the transition metal halides employed in the so-called Zeigler catalysts, are discussed in the Kirk-Othmer publication referred to above and in U.S. Pat. Nos. 4,078,832, 3,987,123, 4,086,062 and 4,008,360, all of which are incorporated herein by reference in their entireties. For instance, at page 856 of Volume 12, Kirk-Othmer describes the complex of hydrochloric acid with aluminum trichloride. The transition metal halide component of the conjugate acid Friedel-Crafts catalysts of this invention can comprise halides of any transition metal, particularly the halides of aluminum, vanadium, boron, titanium, tin, gallium, and combinations thereof. The halide component can be selected from chloride, bromide, fluoride and iodide, although the iodides are less active for the promotion of acid-catalyzed organic reactions and, accordingly, are less preferred. The conjugate Friedel-Crafts catalysts of this invention can comprise equi-molar amounts of the mono-adduct of sulfuric acid plus the transition metal halide, or they can comprise an excess of either one of these two components. It is presently preferred, however, that the conjugate acid contain about 0.1 to about 2 moles of transition metal halide for each mole of the mono-chalcogen compound-sulfuric acid adduct.

The useful chalcogen compound-sulfuric acid components can be produced by the reaction of the chalcogen compound with sulfuric acid by the methods described in my copending application Ser. No. 318,629 filed Nov. 5, 1981, now U.S. Pat. No. 4,445,925, the disclosure of which is incorporated herein by reference in its entirety. That patent describes, in part, the manufacture of urea-sulfuric acid components which are free of decomposition products of urea, sulfuric acid, and the mono- or diurea sulfuric acid adduct, and are particularly preferred for producting the chalcogen compound-sulfuric and components of this invention. As described in U.S. Pat. No. 4,445,925, the reaction of urea and sulfuric acid is extremely exothermic and, if not adequately controlled, can result in the decomposition of reactants or products and the formation of decomposition products such as sulfamic acid, ammonium sulfamate, ammonium sulfate, and other materials. Reactions of sulfuric acid with other chalcogen compounds useful in this invention are also exothermic, and similar precautions should be observed, particularly in the manufacture of more concentrated solutions and melts. The formation of such decomposition products, and the presence of such decomposition products in the compositions and methods of this invention, is unpreferred for several reasons. Such decomposition products may interfere with the acid-catalyzed conversion of organic compounds, or may result in impurities in the finished product. Decomposition also results in the loss of active sulfuric acid which must be available to combine with the useful chalcogen compounds to produce the active monoadduct of sulfuric acid.

Solid chalcogen compound-sulfuric acid components useful in producing the melts and solutions of this invention can be obtained by crystallization from their respective aqueous solutions, as described for urea-sulfuric acid components in my copending application Serial No. 444,667, "Methods for Controlling Vegetation," filed Nov. 26, 1982 and my copending application Ser. No. 673,508 filed Nov. 20, 1984 for "Thermally Stable Urea-Sulfuric Acid Compositions and Methods of Manufacture," the disclosures of which are corporated herein by reference in their entireties. The surfactant, when present, will either crystallize (as described in Ser. No. 444,667) at approximately the same temperature as the chalcogen compound-sulfuric acid component or will be entrained with the crystallized sulfuric acid adduct. In the alternative, the surfactant can be added, when desired, to the dry or damp, crystallized chalcogen compound-sulfuric acid component by any suitable mixing technique.

As described in my copending application Ser. No. 444,667, the urea-sulfuric acid aqueous solution there referred to as 18-0-0-17 has a crystallization temperature of 50° F. Designations such as 18-0-0-17 are conventionally used in the agricultural industry to define the weight percentages of nitrogen, phosphorus, potassium and a fourth component, in this case sulfur, contained in a composition. Thus 18-0-0-17 contains 18 weight percent nitrogen as urea, 0 percent phosphorus, 0 percent potassium, and 17 weight percent sulfur. The 18-0-0-17 solution has a urea/sulfuric acid molar ratio of about 1.2 and contains about 90 weight percent of a combination of urea and sulfuric acid. Urea and sulfuric acid, in combination, constitute 80 weight percent of the aqueous solution designated as 10-0-0-19 in copending application Ser. No. 444,667, which composition has a urea/sulfuric acid molar ratio of about 0.6 and which crystallizes at about 42° F. The aqueous solution designated as 9-0-0-25 comprises approximately 96 weight percent of a combination of urea and sulfuric acid, has a urea/sulfuric acid molar ratio of about 0.4, and crystallizes at 14° F. The indicated crystallization temperatures of the three urea-sulfuric acid aqueous solutions referred to immediately above, and the crystallization temperatures for other formulations of urea and sulfuric acid useful in the composition and methods of this invention, are illustrated, in part, by the isotherms in the ternary phase diagram for urea, sulfuric acid and water in the drawing accompanying copending application Ser. No. 444,667. The crystallization temperatures for other urea-sulfuric acid combinations and for combinations of sulfuric acid and other chalcogen compounds useful in the compositions and methods of this invention can be determined from that drawing or by cooling the selected solution until crystallization occurs. The crystallized material can be separated from the supernatant aqueous phase by any suitable solid-liquid separation technique such as filtration, centrifugation, decanting, and the like, and the recovered damp solid can be dried by evaporation if desired.

Since lower crystallization temperatures are required to separate the desired chalcogen compound-sulfuric acid component from the more dilute solutions, it is preferable to begin with more concentrated solutions having higher crystallization points such as the 18-0-0-17 urea-sulfuric acid compositions which contains only about 10 percent water. More concentrated solutions, and those having higher crystallization temperatures, e.g., 77° F., are even more preferred since less cooling is required to obtain a similar quantity of the chalcogen compound-sulfuric acid component.

Substantially anhydrous solid compositions can be obtained by washing the dried, crystallized chalcogen compound-sulfuric acid component with a strongly hydrophillic solvent such as absolute ethanol or acetone. Ten to 100 weight parts solvent per weight part solute are usually adequate for this purpose. The procedures for making substantially anhydrous urea-sulfuric acid components which contain about one weight percent water or less and are more thermally stable than more hydrous compositions are discussed in my copending application Ser. No. 673,508 referred to above. Such procedures can be employed to make other thermally stable, anhydrous chalcogen compound-sulfuric acid components useful herein.

The anhydrous mono-adduct-containing components are stable at ambient conditions and have negligible vapor pressure up to their decomposition temperatures of up to 300° F. However, they decompose explosively at much lower temperatures in the presence of water. For instance, the hydrous urea-sulfuric acid compositions decompose at 176° F.

The most preferred solid urea composition consisting of the 1/1 urea/sulfuric acid molar adduct has a melting point of about 100° F., and the melting point of the urea-sulfuric acid component increases as the urea/acid ratio deviates from 1:1 in either direction in a manner paralleling the isotherms illustrated in the drawing of Ser. No. 444,667.

Liquid chalcogen compound-sulfuric acid compositions employed in the methods of this invention can be produced by any method capable of producing a solution of the desired composition. Thus, the surfactant and/or other components, when used, can be added to the concentrated chalcogen compound-sulfuric acid solution during or immediately after its manufacture by the process described in my copending application Ser. No. 318,624, referred to above, or such components can be added to the chalcogen compound-sulfuric acid solution prior to its use to catalyze organic reactions in accordance with the methods of this invention. Alternatively, the optional components, when employed, can be mixed with the selected solvent before or concurrently with the solid or concentrated chalcogen compound-sulfuric acid component. Of course, dissolution of the solid chalcogen compound-sulfuric acid compositions described above that contain the desired optional components in the selected solvent will also result in the formation of the active liquid compositions of this invention. The melts employed in several embodiments of this invention can be produced simply by melting the selected solid composition, either prior to or during contact with the organic material to be converted as described hereinafter.

The conjugate Friedel-Crafts acids of this invention can be prepared by reacting the chalcogen compound-sulfuric acid component with one or more transition metal halides. The reaction can be conducted by dissolving the chalcogen compound-sulfuric acid component in a polar solvent such as those described above and dissolving or dispersing the transition metal halide in the resulting solution. Agitation and elevated temperatures, such as temperatures within the range of about 90° to about 150° F., increase the rate of formation of the conjugate acid, i.e., the combination of the mono-adduct and transition metal halide.

The reactant-containing compositions of this invention can be prepared by mixing one or more organic and/or inorganic reactants, such as those discussed hereinafter, with one or more of the chalcogen compound-sulfuric acid components useful in the methods of this invention, including the conjugate Friedel-Crafts catalysts of this invention, in the presence or absence of an added solvent or surfactant. These compositions can be either homogeneous solutions or heterogeneous mixtures including liquid-liquid, solid-liquid and vapor liquid mixtures of the chalcogen compound-sulfuric acid and/or conjugate acid components and one or more liquid, solid or vaporous reactants.

The novel methods of this invention involve acid-catalyzed reactions of organic compounds in the presence of a catalytically active amount of the described chalcogen compound-sulfuric acid components in the presence or absence of additional components such as surfactants, transition metal halides, and/or the conjugate Friedel-Crafts catalysts of this invention, and reference to the chalcogen compound-sulfuric acid components in the description of the methods of this invention is intended to include compositions which contain such additional components. The novel solvent and/or surfactant-containing compositions are preferred in reactions involving relatively lipophilic organic materials since surfactants accentuate the activity of the chalcogen compound-sulfuric acid component toward such materials.

Any organic reaction that is catalyzed by relatively strong acids such as sulfuric acid can be carried out by the methods of this invention. A variety of such reactions are well known in the literature and many are discussed in the Kirk-Othmer Encyclopedia of Chemical Technology publication referred to above and the references referred to therein, the disclosures of which are incorporated herein by reference in their entireties. Illustrative of such acid-catalyzed reactions are (1) oxidation, such as oxidative addition reactions; (2) reduction, such as reductive addition reactions; (3) esterification; (4) transesterification; (5) hydrogenation; (6) isomerization, including racemization of optical isomers; (7) hydrolysis which, for the purposes of this disclosure, includes alcoholisis and thiolosis, i.e., the reaction of organic compounds with alcohols and thiols; (8) alkylation; (9) polymerization of olefinically unsaturated organic compounds; (10) Friedel-Crafts reactions; (11) demetalization; and (12) nitration reactions. Other reactions that are known to be catalyzed by acid catalysts can also be catalyzed by the chalcogen compound-sulfuric acid components described herein. The specific methods discussed hereinafter can be catalyzed by any one of the chalcogen compound-sulfuric acid catalyst components discussed above including the surfactant and/or transition metal halide-containing components.

Acid-catalyzed oxidative reactions primarily involve the abstraction of hydrogen from an organic compound by reacting the compound with an oxidant. An illustrative example of such reactions is the oxidative addition of organic compounds illustrated by the following expression:

$$R_1H + R_2H + \tfrac{1}{2}O_2 \rightarrow R_1R_2 + H_2O \tag{1}$$

wherein $R_1$ and $R_2$ are the same or different hydrocarbyl radicals including straight and branched chain alkanes; alkenes; alkynes, aromatics; alkyl-, alkenyl-, and alkynyl-substituted aryls; and aryl-substituted alkanes, alkenes and alkynes, of essentially any molecular weight, but usually having from 1 to about 40 carbon atoms per molecule. Preferred reactants include olefins, particularly alpha-olefins.

The acid-catalyzed oxidation reactions can be promoted by contacting the organic compound to be converted with the catalyst component in the presence of an oxidant, which is preferably oxygen as illustrated in the above equation. The oxidative addition reaction illustrated in the equation requires only that the organic compound contain a carbon-to-hydrogen bond capable of undergoing oxidative addition reactions. The organic compound can be either dispersed or dissolved in a melt or solution of the catalyst component in an appropriate solvent, or it can be contacted with the catalyst component by conventional mixing and contacting procedures.

Acid-catalyzed reduction reactions of organic compounds in accordance with the methods of this invention may involve the addition of hydrogen to unsaturated organic compounds. Illustrative reactions include the hydrogenation of organic compounds containing olefinic, alkynyl or aromatic unsaturation, and reductive addition reactions such as dimerization, oligermerization and polymerization reactions as illustrated schematically in the following expression:

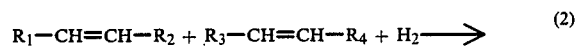
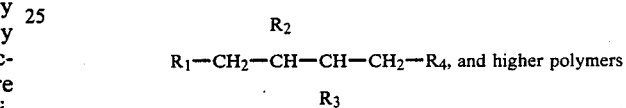

wherein $R_1$, $R_2$, $R_3$ and $R_4$ are the same or different functional groups selected from hydrogen and alkyl moieties having from 1 to about 20 carbon atoms. Preferred reactants including normal and branched chain alkenes and alkenyl aromatic compounds. The acid-catalyzed reduction reactions can be conducted by contacting the organic compound to be converted with a reducing agent such as hydrogen, hydrazine, and/or other reducing agents, in the absence of oxidants. Such reactions can be carried out by forming a composition such as a melt, solution or dispersion containing the unsaturated organic compounds, the reducing agent, and the chalcogen compound-sulfuric acid component in the absence of oxidants under conditions of temperature and pressure sufficient to promote the reductive addition reaction. As illustrated by the examples discussed hereinafter, the reductive addition of propylene can be promoted at ambient temperature.

Acid-catalyzed esterification reactions in accordance with the methods of this invention typically involve reacting an esterifiable organic compound having one or more amide, nitrile, carboxylic acid, carboxylic acid anhydride, acyl halide, and/or thiocarboxylic acid groups, with an organic alcohol or thiol in the presence of the acid catalyst component. Such reactions can be conducted by contacting a composition containing the chalcogen compound-sulfuric acid catalyst component, one or more esterifiable organic compounds, and one or more alcohols, thiols and/or amines, under esterification conditions. Reactions of acids, amides and thioacids are illustrated by the following expression:

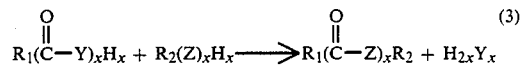

wherein $R_1$ and $R_2$ are any organic radicals including natural and synthetic polymers such as partially hydrolyzed protein or cellulose, nylon, dacron, etc., and Y and Z are the same or different divalent radicals selected from oxygen, sulfur and NH groups. X is any integer of 1 or greater and can range up to 1000 or more, depending upon the molecular weight of the compound involved. For instance, partially hydrolyzed polymers such as those referred to above can contain 100 or more functional groups capable of undergoing esterification by the acid-catalyzed methods of this invention.

The reactions of alcohols, thiols, and amines with organic cyanides and acyl halides, while not illustrated in expression (3) above, are well-known and can be promoted by the methods of this invention. For instance, the reaction of alcohols with acyl chlorides may be catalyzed by the method of the invention to form the corresponding ester and hydrogen chloride, and the reaction of organic cyanides with water and/or alcohols results in the formation of the corresponding ester and ammonia as discussed in Kirk-Othmer, Vol. 9, page 302. The evolution of ammonia by esterification of nitriles and amides may result in the consumption of some of the sulfuric acid in the catalyst component but will not prevent the occurrence of acid-catalyzed esterification. Sulfuric acid consumed by ammonia or by other bases produced or present in esterification reactions (or in other acid-catalyzed reactions encompassed by the methods of this invention) can be replaced by adding makeup sulfuric acid during the process if desired.

Although expression (3) above indicates that all of the acyl moieties are associated with one organic radical indicated by $R_1$, and that all of the alcohol, thiol and/or amine moieties are associated with one organic radical identified as $R_2$, that form of expression is employed only in way of illustration. For instance, a multifunctional carboxylic acid can be esterified by a number of monofunctional alcohols; conversely, a number of monofunctional carboxylic acids, thio-acids, etc., can be esterified by fewer molecules of a polyfunctional alcohol, thiol, etc.

Essentially any transesterification reaction can be conducted by the methods of this invention including (a) ester-ester interchange, (b) alcoholisis, which involves exchange of alcohol, thiol or amino groups, and (c) acidolysis which involves interchange of carboxylic acid, thiocarboxylic acid and/or amide groups. Such transesterification reactions can be conducted by contacting a composition containing (1) the chalcogen compound-sulfuric component useful in this invention, (2) a carboxylic acid ester, thioester, and/or amido-ester, and (3) either (a) a dissimilar organoester, thioester and/or amide-ester, (b) a carboxylic acid, thioacid, or amide, (c) an alcohol, thiol, and/or amine, or (d) combinations of (a), (b) and (c), under esterification conditions. Such reactions are illustrated schematically by the following expressions:

(a) ester-ester interchange

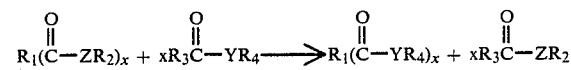

(b) alcoholisis

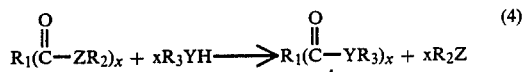

(c) acidolosis

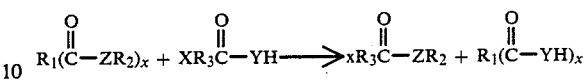

As in the case of esterification illustrated by expression (3) above, the $R_1$, $R_2$, $R_3$ and $R_4$ moieties involved in expressions 4(a), (b), and (c) can be the same or different organic moieties of essentially any molecular weight, Y and Z are the same or different divalent radicals selected from oxygen, sulfur and NH groups, and x represents any integer of 1 or greater. Also, as in the case of esterification, compounds containing one or more ester groups can be reacted either with mono- or polyfunctional esters, alcohols, thiols, acids, thioacids, etc. For instance, alcohols such as 1-butanol can be reacted with either simple esters such as ethyl acetate to produce butylacetate, or with complex polyamides, such as proteins, to produce the corresponding butyl esters of aminoacids contained in the protein.

The acid-catalyzed hydrogenation reactions of this invention can be conducted by contacting a composition containing (1) an organic compound containing carbon-to-carbon unsaturation, (2) hydrogen, and (3) the chalcogen compoundsulfuric acid-containing catalyst under hydrogenation conditions. The reaction can be conducted by exposing a composition containing the acid catalyst component, hydrogen, and an unsaturated organic compound under conditions of temperature and pressure sufficient to promote hydrogenation. The hydrogenation of olefins is illustrated by expression (5).

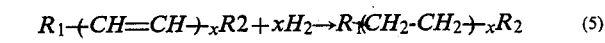

wherein $R_1$ and $R_2$ are the same or different hydrogen or organic moieties of essentially any molecular weight and x is any integer of 1 or greater. For example, the methods of this invention can be employed to hydrogenate ethylene as well as polymers having molecular weights of 100,000 or greater, which polymers contain a plurality of olefin bonds. They can also be employed to hydrogenate benzene, alkyl or alkenyl aromatics, alkynes, and other unsaturated organic compounds. Olefinically unsaturated organic compounds, particularly hydrocarbon compounds, having 2 to about 40 carbon atoms are presently preferred. The hydrogenation reactions can be promoted by hydrogen, hydrazine, or other hydrogenating agents and are preferably conducted in the absence of oxidizing agents such as oxygen and other oxidants.

The acid-catalyzed isomerization reactions involve the isomerization of any organic compounds having 4 or more carbon atoms by contacting such compounds with the useful acid-catalyst component under isomerization conditions. Such isomerization reactions can be conducted by contacting a composition containing the acid catalyst component and one or more isomerizable organic compounds under isomerization conditions. Essentially any organic compounds can be isomerized by the methods of this invention including hydrocarbons and organic compounds containing elements other than carbon and hydrogen such as oxygen, sulfur, phosphorus, nitrogen, and the like. The existence of functional groups in organic compounds employed in the acid-catalyzed isomerization reactions of this invention which are reactive in the presence of the acid catalyst component may result in the occurrence of other reactions in addition to isomerization. Nevertheless, isomerization will also occur.

The isomerization reactions encompassed by the methods of this invention are particularly useful for the isomerization of relatively low molecular weight hydrocarbons having 4 to about 20 carbon atoms per molecule. They are also useful for the racemization of optical isomers, i.e., the conversion of dextro- or levorotatory isomers to the corresponding racemic mixture.

The acid-catalyzed hydrolysis reactions include the reaction of water, alcohols, on thiols, with (a) carboxylic acid amidoesters including polyamides; (b) carboxylic acid esters and polyesters such as proteins, i.e., polyamino acid esters; (c) thiocarboxylic acid esters and polyesters; (d) ethers and thioethers including polyoxyethers and thioethers such as cellulose, rayon, starches, and other polysaccharides; (e) di- and poly-alkylamines including polyamines; (f) organic compounds containing olefinic unsaturation; and (g) epoxides. Such hydrolysis reactions can be conducted by contacting a composition containing (1) the chalcogen compound-sulfuric acid component, (2) an organic compound having one or more hydrolyzable functional groups such as amido ester, acid ester, thioester, ether, thioether, amino, olefinic, and/or epoxy linkages, and (3) a hydrolyzing compound such as water, alcohols and/or thiols under conditions of temperature and pressure sufficient to promote hydrolysis of the hydrolyzable functional group. In the alternative, the organic compound containing a hydrolyzable functional group such as amido ester, acid ester, etc., can be contacted with a composition containing the chalcogen compound-sulfuric acid-containing acid catalyst and a hydrolyzing compound under hydrolyzing conditions.

Several of the hydrolysis reactions encompassed by this embodiment of the invention are also encompassed by the transesterification methods of this invention which involve alcoholysis as discussed above. Such reactions include the reaction of alcohols and/or thiols with (1) mono- or polycarboxylic acid esters or polyesters; (2) mono- or polyfunctional thiocarboxylic acid esters or polyesters; and (3) mono-/ or polycarboxylic acid amido-esters or polyamido esters.

A particularly interesting aspect of the hydrolysis reactions which can be effected in accordance with the methods of this invention is that they can be employed for either the partial or the complete hydrolysis of natural and synthetic polymers such as polysaccharides including cellulose, starches, and the like, protein, rayon, nylon, and others, by contacting such materials with the acid catalyst components of this invention containing water. Such reactions proceed even at ambient temperature and, if allowed to go to completion, they result in complete depolymerization, i.e., complete hydrolysis of the polymer. For example, cellulose can be converted completely to glucose and proteins can be converted to amino acids by this method. Hydrolysis of polysaccaharides is discussed in more detail in my copending application Ser. No. 673,358 referred to above the disclosure of which is incorporated herein by reference in its entirety. The partial hydrolysis of cellulose appears to account for the dramatic herbicidal activity of the chalcogen compound-sulfuric acid components employed in the methods of this invention, and the herbicrdal activity of urea-sulfuric acid components is discussed in more detail in my copending application Ser. No. 444,667. The ability of surfactants to accentuate the activity of the urea-sulfuric acid component and to broaden the variety of vegetation controlled is also discussed in said copending application. The other chalcogen compound-sulfuric acid components exhibit similar herbicidal activity when combined with surfactants.

The hydrolysis reactions are illustrated, in part, by the following expressions which are intended only to be schematic representations of several of the acid-catalyzed hydrolysis reactions encompassed by the methods of this invention:

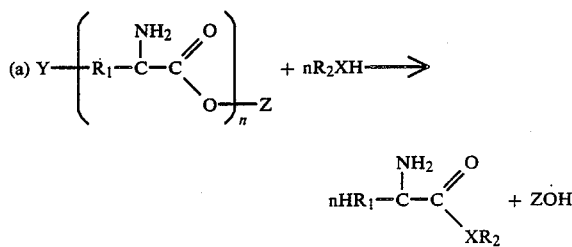

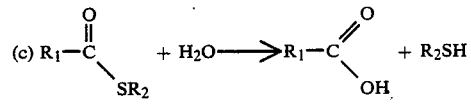

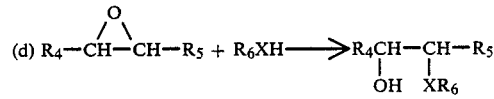

Expression 6(a) represents the complete acid-catalyzed hydrolysis of amino acid esters, including polyamino acid esters such as proteins, by reaction with a hydrolyzing agent. In accordance with expression 6(a), $R_1$ can be any difunctional organic moiety, Y can be hydrogen or a mono-functional terminal inorganic moiety such as potassium or other metal ion, $R_2$ is hydrogen or any organic moiety including hydrocarbyl radicals having 1 to 20 carbon atoms per molecule; X is oxygen, sulfur, or a combination of these, and n is any integer of 1 or greater. From expression 6(a) it can be seen that the reaction of protein—a poly-alphaamino acid ester—with water, if allowed to go to completion, results in formation of the amino acid monomer units contained in the protein. Expression 6(b) illustrates the hydrolysis of a diorganoamine by reaction with an organ-thiol in which $R_1$, $R_2$, and $R_3$ can be any organic moiety.

Expression 6(c) illustrates the hydrolysis of an organic thioester by reaction with water to produce the corresponding carboxylic acid and thiol in which $R_1$ and $R_2$ can be any organic moiety. As in the case of the other hydrolysis reactions encompassed by this embodiment of the invention, alcohols and/or, thiols can be substituted for, or combined with, the water illustrated in expression of 6(c).

Expression 6(d) schematically illustrates the hydrolysis of an organic epoxide by the acid-catalyzed reaction of the epoxide with water, thiols, or alcohols, in which $R_4$ and $R_5$ are monovalent moieties selected from hydrogen and any organic moiety, $R_6$ is a monovalent organic moiety having at least one carbon, and X is selected from oxygen, sulfur and nitrogen.

The hydrolysis of olefins, including poly-functional olefins, with water, alcohols on, thiols, can be illustrated schematically by the following expression:

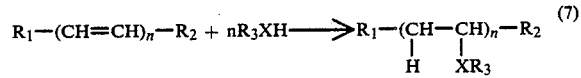
(7)

in which $R_1$ and $R_2$ and $R_3$ are the same or different monovalent moieties selected from hydrogen and any organic moiety, X is O, S, and/or NH, and n is any integer of 1 or greater.

Alkylation reactions in accordance with the methods of this invention include the reaction of any organic compound capable of being alkylated by acid-catalyzed reaction with an organic reactant containing olefinic unsaturation. These reactions can be effected by contacting the alkylatable organic compound with a composition comprising the chalcogen compound-sulfuric acid-containing acid catalyst and an organic reactant containing olefinic unsaturation, and are illustrated schematically by the following expression:

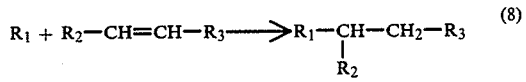
(8)

wherein $R_2$ and $R_3$ are the same or different hydrogen or organic moieties, particularly alkyl groups having from 1 to 10 carbon atoms, and $R_1$ is an alkylatable organic compound, particularly straight or branched chain alkanes, aromatics, alkyl-aromatics, and/or aryl-alkanes having from 4 to 20 carbon atoms per molecule.

Acid-catalyzed olefin polymerization reactions include the polymerization of at least one organic compound containing at least one carbon-to-carbon olefin bond capable of undergoing acid-catalyzed polymerization by contacting the organic compound or compounds with the sulfuric acid-containing catalyst of this invention. In this embodiment, the reaction system is preferably substantially oxidant-free. Such polymerization reactions are illustrated schematically by the following expression:

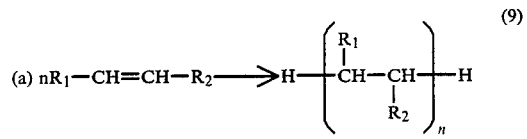
(9)

in which $R_1$ and $R_2$ are selected from hydrogen or monovalent organic moieties, particularly hydrocarbyl radicals having from to 10 carbon atoms, and n is the number of monomer units incorporated in the polymer. Copolymers of two or more olefinically unsaturated monomers can be produced. Illustrative of such copolymers are styrene-butadiene, ethylene-propylene, methacrylic acid-ethyl acrylate-hydroxyethylacrylate, and ethylene-dicyclopentadiene copolymers, and the like, including the so-called hydrocarbon resins derived from cracked petroleum distillates, turpentine fractions, coal tar fractions and certain olefinic monomers, such as the hydrocarbon resins discussed in Kirk-Othmer, Volume 2, at pages 852-857 and in the references cited therein.

The Friedel-Crafts reactions involve the reaction of organic compounds, particularly hydrocarbon compounds, capable of undergoing acid-catalyzed Friedel-Crafts reactions, with hydrocarbyl halides. Such reactions can be effected by contacting one or more organic compounds with a composition comprising the sulfuric acid-containing catalyst and a hydrocarbyl halide. Such Friedel-Crafts reactions are illustrated schematically by the following expression:

$$R_1H + R_2X \rightarrow R_1R_2 + HX \qquad (10)$$

in which $R_1$ is a monovalent organic moiety capable of undergoing Freidel-Crafts reactions with hydrocarbyl halides, $R_2$ is a monovalent hydrocarbyl moiety, preferably an alkyl group having from 1 to 20 carbon atoms, and X is a halogen, preferably chlorine, bromine or fluorine, most preferably chlorine.

The acid-catalyst component employed to catalyze the Friedel-Crafts reactions can comprise any of the described chalcogen compound-sulfuric acid components, although the acid components which contain a Friedel-Crafts halide catalyst such as the novel conjugate Friedel-Crafts catalysts of this invention, are preferred.

The acid-catalyzed demetalization reactions include the demetalization of organo-metal compounds capable of undergoing acid-catalyzed demetalization by reaction with water and/or alcohols, and they can be effected by contacting a composition containing such organo-metal compounds, the described sulfuric acid-containing catalyst and water and/or alcohols, under conditions of time and temperature sufficient to obtain the desired degree of demetalization. Such demetalization reactions are illustrated by the following expression:

$$R_aM^a + aH^+ \rightarrow aRH + M^{+a} \qquad (11)$$

wherein R is any organic radical including porphyrins and petroporphyrins, M is any metal, and a is the valence of the metal associated with the organic moiety. Organic complexes of zero-valent metals can also be demetalized by these methods. Illustrative of the organo-metal compounds that can be demetalized by reaction with water and/or alcohol in accordance with these methods are the porphyrins and petroporphyrins commonly found in petroleum crudes, tar-sand oils, shale oils, coal extracts, and the like.

The acid catalyzed demetalization reactions can be conducted in the presence of an oxidant such as oxygen, peroxides, ozone, and the like, to oxidize the metal contained in the organo-metal compound to a more soluble, higher valence state when desired. Such oxidative demetalization conversions can be effected by contacting a composition containing the organo-metal compound, the chalcogen compound-sulfuric acid component, and the oxidant. Similarly, the valence state of the metal complexed in the organo-metal compound can be reduced to produce a more soluble metal ion, e.g., the conversion of ferric to ferrous iron, by conducting the acid-catalyzed demetalization reaction in the presence of a reducing agent such as hydrogen, hydrazine, and the like. Such reductive acid-catalyzed demetalization reactions can be conducted by contacting a composition containing the organometal compound, the chalcogen compound-sulfuric acid component, and a reducing agent.

The acid-catalyzed nitration reactions of this invention involve the reaction of organic compounds capable of undergoing acid-catalyzed nitration with nitrogen oxides, particularly with nitric oxide, and can be effected by contacting a composition containing the nitratable compound, nitrogen oxides, and the chalcogen compound-sulfuric acid-containing catalyst under nitration conditions. Such reactions are illustrated schematically by expression (12).

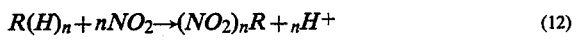

(12)

in which R is any nitratable organic moiety having a valence of n. Illustrative of nitration reactions that be conducted in accordance with this invention are the reaction of toluene with nitric oxide to produce nitrotoluene and trinitrotoluene (TNT), the nitration of cellulose to produce nitrocellulose, the nitration of alkanes such as n-decane, and the like.

The acid-catalyzed organic reactions discussed above, and other acid-catalyzed reactions known in the art, can be effected by contacting the organic material to be reacted in either vapor phase, liquid phase, or solid phase (as in the case of cellulose, nylon and other solid material), with the liquid or solid chalcogen compound-sulfuric acid-containing catalyst. The liquid catalysts can comprise a melt of the anhydrous chalcogen compound-sulfuric acid catalyst component, or it can comprise a solution of that component in either the organic feed material or other solvent. The solid catalysts can comprise the chalcogen compound-sulfuric acid component, with or without the described optional components, impregnated or ion-exchanged into a solid support. Mixed liquid phase reactions can be conducted by forming emulsions or dispersions of the chalcogen compound-sulfuric acid component melt or solution and the reactants and/or organic material to be converted. The novel surfactant-containing chalcogen compound-sulfuric acid components of this invention are particularly suitable for use as acid catalysts in the conversion of organic materials containing significant amounts of lipophilic substances such as waxes, oils, and high molecular weight organic substances. Illustrative of such lipophilic materials are the waxy cuticle on many types of vegetation, proteins, particularly fat-containing proteins, cellulosic substrates containing ligands and other lipophilic substances derived from wood, and the like.

The acid-catalyzed reactions of this invention can be conducted at any temperature below the thermal decomposition temperature of the chalcogen compound-sulfuric acid component and above that temperature at which the composition comprising the chalcogen compound-sulfuric acid component solidifies. The reaction temperature should also be maintained below the temperature at which the organic feed material, reactants, intermediates, or products react with the chalcogen compound-sulfuric acid component. The occurrence of any such side reactions at any given reaction temperature can be readily determined by analyzing the product to determine the presence of by-products resulting from such side reactions. For instance, reaction temperatures used with the urea-sulfuric acid components should be maintained below 176° F. and preferably below about 170° F. in reactions in which a significant amount of water is present due to the relatively low decomposition temperature of the urea-sulfuric acid component in the presence of water. Higher reaction temperatures up to about 300° F. can be employed with urea-sulfuric acid components under anhydrous conditions when the reaction system is substantially free of water, i.e., when the system contains less than about 2, preferably less than about 1 weight percent water based on the concentration of urea-sulfuric acid component. However, such higher temperatures, i.e., temperatures above 170° F., are preferably avoided unless the reaction system is essentially water-free, i.e., does not contain any detectable amount of water. Reaction rate increases as temperature is increased. The thermal decomposition temperature of other hydrous and anhydrous chalcogen compound-sulfuric acid components can be readily determined by gradually increasing the temperature of the selected composition until evidence of decomposition occurs such as effervescence or other vapor evolution and discoloration.

The methods of this invention can be conducted at essentially any pressure and even under vacuum if desired. Vapor phase reactions, i.e., reactions involving organic reactants in the vapor phase, can be accelerated by increasing the pressure on the system. Illustrative reaction pressures are 0 to 2,000 atmospheres although pressures of 0 to 100 atmospheres are usually sufficient to achieve acceptable reaction rates.

The acid-catalyzed reactions of this invention require contact times of the organic reactants and the sulfuric acid-containing component commensurate with the desired product yield. Generally, increasingly the contact time increases the conversion. Since reaction rate depends upon the nature of the reaction involved, the compatibility of the sulfuric acid-containing component with the reactants, and the operating pressure and temperature, the reaction time should be sufficient to obtain the degree of conversion required. Batch contact times of one minute to 100 hours are usually sufficient to accomplish complete conversion of most organic substrates. Shorter reaction times will usually be involved in continuous processes employing the methods of this invention in which case it may be desirable to separate unreacted organic materials from the effluent of the reaction zone and to recycle those materials to the reaction zone.

The novel compositions and acid-catalyzed methods of converting organic compounds in accordance with this invention have several significant advantages over compositions and methods otherwise available to the art. The chalcogen compound-sulfuric acid components are relatively inexpensive; in addition, they are non-corrosive and stable under normal conditions. They are also highly active protonating agents and therefore can be employed to effect the acid-catalyzed conversion of a wide variety of organic compounds without promoting reactions associated with other acid catalysts, particularly side reactions associated with the use of sulfuric acid such as oxidation and sulfonation.

The invention is further described by the following examples which are illustrative of specific modes of practicing the invention and are not intended as limiting the scope of the invention as defined by the appended claims.

EXAMPLE 1

This example illustrates the hydrolysis of complex polyethers by demonstrating the complete hydrolysis of cellulose to glucose in the presence of a urea-sulfuric acid component of this invention. Sterile cotton swabs are dissolved in a urea-sulfuric acid component having a urea/sulfuric acid molar ratio of 1.2 and containing 38.6 weight percent urea, 52.1 weight percent sulfuric acid, and 8.3 weight percent water which is maintained at a temperature of 70° F. The cotton swabs are added sequentially to approximately 500 ml. of the described urea-sulfuric acid component, and the mixture is stirred throughout the operation. Complete dissolution of each cotton swab occurs in approximately one minute. After the addition of approximately 20 cotton swabs the mixture become more viscous. A quantity of the reactant mixture is analyzed by high precision liquid chromatography (HLPC) and is found to contain glucose in an amount which corresponds to the stoichiometric conversion of the cellulose feed to the reaction. Neither the HLPC analysis nor any other observation during the operation indicates the occurrence of any reaction other than the hydrolysis of cellulosic to glucose. There is no evidence of sulfonation or oxidation of either the cellulose or glucose. No fumes are emitted and the reaction medium does not discolor during the process.

EXAMPLE 2

This example illustrates the use of a urea-sulfuric acid component of this invention to acid-catalyze the hydrolysis of cellulose in living vegetation and the consequent efficacy of the chalcogen compound-sulfuric acid components as herbicides.

Four replicated test plots of five acres each comprising onions at the first true-leaf stage (approximately one-inch high) infested with malva, cheese weed, nightshade, shephards purse, peneapple weed and purslane, are each treated by foliar application of 50 gallons per acre of a urea-sulfuric acid component having a urea/sulfuric acid molar ratio of approximately 1.1 and containing 14.6 weight percent urea, 20.8 weight percent sulfuric acid and 64.6 weight percent water. The described treatment results in 95 to 100 percent kill of all weed species within 48 hours after application. There is no damage to the onion crop as evidenced by the lack of foliage browning, spotting, or the like. The cellulosic structure of the onion crop is protected by the waxy cuticle characteristic of green onions, which, however, can also be hydrolyzed by the use of the surfactant-containing chalcogen compound-sulfuric acid components within the scope of this invention.

EXAMPLE 3

This example illustrates the hydrolysis of polycarboxylic acid esters and demonstrates the depolymerization of protein by contact with the chalcogen compound-sulfuric acid components of this invention. Two cowhide pump seals are contacted with a urea-sulfuric acid component containing 36.5 weight percent urea, 52.1 weight percent sulfuric acid and 11.4 weight percent water having a urea/sulfuric acid molar ratio of about 1.1 for approximately 70 hours at room temperature. The cowhide seals completely dissolve within the 70-hour contact period.

EXAMPLE 4

The operation of Example 3 is repeated by contacting two cowhide pump seals with a urea-sulfuric acid component containing 21.5 weight percent urea, 55.2 weight percent sulfuric acid and 23.3 weight percent water having a urea/sulfuric acid molar ratio of about 0.6. This composition corresponds to the formulation 10-0-0-18. The cowhide pump seals completely dissolve within 70 hours at room temperature.

EXAMPLE 5

This example illustrates the oxidative addition of organic compounds and demonstrates the oxidative addition of propylene in the presence of the chalcogen compound-sulfuric acid components of this invention. Technical grade propylene and air are introduced into approximately 1000 ml. of a urea-sulfuric acid component containing 38.6 weight percent urea, 52.1 weight percent sulfuric acid and 9.3 weight percent water having a urea/sulfuric acid molar ratio of 1.2. The gas mixture is introduced through a sparger submerged in the urea-sulfuric acid component which is maintained at 70° F. and is contained in a three-neck five-liter flask provided with agitation, and feed inlet and exit means. The vapor effluent from the liquid phase is removed from the five-liter flask and passed to an ice-cooled liquid trap in which the reaction products are collected. The liquid phase recovered from the vapor effluent is analyzed by infrared spectroscopy and is found to contain propylene dimers and higher oligimers of propylene containing olefinic unsaturation.

EXAMPLE 6

Propylene and butene are reductively added to each other by introducing gaseous propylene and 2-butene into the liquid phase formed by melting an anhydrous urea-sulfuric acid component containing 42.6 weight percent urea and 57.4 weight percent sulfuric acid having a urea/sulfuric acid molar ratio of 1.2. The liquid phase is maintained at a temperature of 150° F. and the vapor and liquid phases are maintained at a pressure of 1000 psig. The liquid phase is continuously removed from the reaction zone and flashed to recover vaporizable dimers and higher polymers of propylene and 2-butene, and co-polymers of propylene and 2-butene. Higher polymers that are not removed by flashing can be extracted from the urea-sulfuric acid melt with normal hexane at a pressure sufficient to maintain the normal hexane in the liquid phase. The recovered urea-sulfuric acid component is recycled to the reaction zone.

EXAMPLE 7

Maleic acid is reacted with 1,2-ethanediol (glycol) by agitating a 50-50 molar mixture of maleic acid and glycol with a urea-sulfuric acid component containing 36.5 weight percent urea, 52.1 weight percent sulfuric acid and 11.4 weight percent water having a urea/sulfuric acid molar ratio of 1.1 at a temperature of 140° F. under a pressure of 100 psig. for 10 minutes to produce the corresponding polyester of maleic acid and 1,2-ethanediol. The resulting polymer is extracted from the reaction phase with isopropyl alcohol.

EXAMPLE 8

Benzene is alkylated with a mixture of 1-butene and 2-butene to produce normal and isobutylbenzenes by agitating a mixture of benzene, 1-butene and 2-butene with a molten urea-sulfuric acid component containing 42.6 weight percent urea and 57.4 weight percent sulfuric acid in the presence of an alkyl phenol polyethylene oxide surfactant at a temperature of 160° F. and under a reaction pressure sufficient to maintain the reactants in the liquid phase. The resulting alkylbenzene is recovered by centrifuging the resultant reaction phase mixture. Complete separation is achieved by washing the urea-sulfuric acid component melt with toluene.

EXAMPLE 9

Normal-butylbenzene is prepared by heating equal molar amounts of 1-chlorobutane and benzene in a molten urea-sulfuric acid component containing 42.6 weight percent urea and 75.4 weight percent sulfuric acid having a urea/sulfuric acid molar ratio of 1.2 at a temperature of 140° F. and a pressure of 100 psig. for a period of 10 minutes. The n-butylbenzene product is recovered by cooling the reaction mixture to solidify the urea-sulfuric acid component melt and extracting the resulting mixture with toluene. The n-butylbenzene product is removed from the toluene solvent by distilling the solvent, and the urea-sulfuric acid component is re-melted and recycled to the process.

EXAMPLE 10

A mixture of isooctanes is prepared by contacting normal octane with a molten urea-sulfuric acid component containing 42.6 weight percent urea and 57.4 weight percent sulfuric acid and having a urea/sulfuric acid molar ratio of 1.2 at a temperature of 160° F. under a pressure of 500 psig. for 5 minutes. The resulting isooctane mixture is recovered by cooling the melt to a temperature of 70° F. to solidify the molten mixture and extracting the isooctane product with normal hexane. The resulting solution of hexane and isooctane is separated by distillation and the urea-sulfuric acid is melted and returned to the reaction zone.

EXAMPLE 11

A petroleum crude oil containing organo-metal compounds comprising petroporphyrins is demetalized by contacting the petroleum crude oil with an aqueous urea-sulfuric acid component containing 36.5 weight percent urea, 52.1 weight percent sulfuric acid and 11.4 weight percent water having urea/sulfuric acid molar ratio of 1.1 in the presence of oxygen at a temperature of 160° F. and a pressure of 500 psig. with sufficient agitation to intimately mix the petroleum crude oil and the urea/sulfuric acid component. The resulting petroleum crude oil of reduced metals content is recovered by decanting from the urea-sulfuric acid component, water washed to remove residual urea, sulfuric acid and metal salts, and dried by distillation.

EXAMPLE 12

Benzene is nitrated by forming a dispersion of benzene in a solution of a urea-sulfuric acid component having a urea/sulfuric acid molar ratio of 1.1 and containing 15.9 weight percent urea and 22.7 weight percent sulfuric acid in water with sufficient agitation to produce an intimate dispersion of the benzene and the urea-sulfuric acid component solution. Nitric oxide is dispersed into the agitated mixture of benzene and the urea-sulfuric acid component, and the resulting mixture is contacted at a temperature of 150° F. and a pressure of 200 psig. The resulting nitrated benzene product is recovered by cooling the reaction mixture and extracting the nitrated benzene product with toluene.

EXAMPLE 13

The mono-N-allyl thioformamide adduct of sulfuric acid is prepared by placing 50 grams of N-allyl thioformamide in a 500 ml. flask along with 200 ml. of diethylether, chilling to 50° F. and then gradually adding 51 grams of 98 percent sulfuric acid pre-chilled to 30° F. at a rate sufficiently slow to maintain the mixture in the flask at a temperature below 50° F. 200 ml. water is added to the flask and the mixture is allowed to equilibrate to room temperature (70° F.). Cotton swabs are then immersed in the mixture at room temperature and maintained for 24 hours to hydrolyze the cotton cellulose.

EXAMPLE 14

21 grams of 98 weight percent sulfuric acid and 50 grams of 1-(4-aminobenzenesulfonyl)-2-thiourea are mixed by the procedure described in Example 13 to produce the corresponding equimolar adduct dissolved in the ether-water mixture which can then be employed to hydrolyze cellulose.

EXAMPLE 15

30 grams of 98 weight percent sulfuric acid and 50 grams of 1-benzoylurea are mixed by the procedure described in Example 13 to form the corresponding equimolar adduct dissolved in the ether-water mixture which can be employed to hydrolyze cellulose.

EXAMPLE 16

15.5 grams of 98 weight percent sulfuric acid and 50 grams of 1,3-bis(2-ethoxyphenyl) carbamide are mixed by the procedure described in Example 13 to form the corresponding equimolar adduct dissolved in the ether-water mixture which can be employed to hydrolyze cellulose as described in Example 13.

EXAMPLE 17

22 grams of 98 weight percent sulfuric acid and 50 grams of 1-(2-bromo-3-methylbutanoyl) carbamide are mixed by the procedure described in Example 13 to produce the corresponding equimolar adduct dissolved in the ether-water mixture which can be employed to hydrolyze cellulose.

EXAMPLE 18

23 grams of 98 weight percent sulfuric acid and 50 grams of 1-(4-bromophenyl) carbamide are mixed by the procedure described in Example 13 to form the corresponding equimolar adduct dissolved in the ether-water solution which can be employed to hydrolyze cellulose a described in Example 13.

EXAMPLE 19

34 grams of 98 weight percent sulfuric acid and 50 grams of 1,3-diacetyl carbamide are mixed by the procedure described in Example 13 to form the corresponding equimolar adduct dissolved in the ether-water solution. Propylene and air are then bubbled through the solution at a temperature of 90° F. and a pressure of 500 psi. to form proplene dimers and higher oligomers.

EXAMPLE 20

32.5 grams of 98 weight percent sulfuric acid and 50 grams of 1-ethyl-2-selenourea are mixed by the procedure described in Example 13 to form the corresponding equimolar adduct dissolved in the ether-water solution. Cowhide pump seals can be emerged in the solution maintained for 24 hours at 100° F. to partially hydrolyze the cowhide protein.

While particular embodiments of this invention have been described, it will be understood, of course, that the invention is not limited thereto since many obvious modifications can be made and it is intended to include within this invention any such modifications as will fall within the spirit and scope of the appended claims.

I claim:

1. A method for carrying out an acid-catalyzed reaction, selected from the group consisting of hydrolysis, alcoholysis, and combinations thereof, by reacting an organic compound having a chemical linkage selected from the group consisting of amido ester, acid ester, thioester, epoxy, and amino linkages, and combinations thereof with a reactant selected from the group consisting of water when said reaction comprises hydrolysis, alcohols when said reaction comprises alcoholysis, thiols when said reaction comprises thiolysis, and combinations thereof, which method comprises the step of conducting said reaction in the presence of a catalytically active amount of the monoadduct of sulfuric acid and a chalcogen-containing compound having the empirical formula

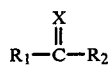

wherein X is a chalcogen, each of $R_1$ and $R_2$ is independently selected from the group consisting of hydrogen, $NR_3R_4$ and $NR_5$, with at least one of $R_1$ and $R_2$ being other than hydrogen, each of $R_3$ and $R_4$ is independently selected from the group consisting of hydrogen and monovalent organic radicals, and $R_5$ is a divalent organic radical, wherein the molar ration of said chalcogen-containing compound to said sulfuric acid is about ¼ to less than 2.

2. The method defined in claim 1 wherein said molar ratio is within the range of about ½ to about 3/2, and said chalcogen is selected from the group consisting of oxygen and sulfur.

3. The method defined in claim 1 wherein said reaction is conducted in the presence of a member selected from the group consisting of surfactants, polar solvents other than water, and combinations thereof.

4. The method defined in claim 1 wherein said reaction is conducted under substantially anhydrous conditions.

5. The method defined in claim 1 wherein said chalcogen-containing compound and sulfuric acid, in combination, constitute at least about 80 weight percent of the mixture of said sulfuric acid, chalcogen compound, organic compound and reactant, said molar ratio is within the range of about ½ to about 3/2, and said mixture is substantially anhydrous and has a melting point about 70° F. and is molten.

6. The method defined in claim 1 wherein said reactant comprises water and said reaction comprises hydrolysis.

7. The method defined in claim 1 wherein at least 1 of $R_1$ and $R_2$ is $NR_3R_4$.

8. The method defined in claim 1 wherein said chalcogen-containing compound is selected from the group consisting of urea, thiourea, formamide, and combinations thereof.

9. The method defined in claim 1 wherein said chalcogen-containing compound comprises urea.

* * * * *

UNITED STATES PATENT AND TRADEMARK OFFICE
CERTIFICATE OF CORRECTION

PATENT NO. : 4,942,254

DATED : July 17, 1990

INVENTOR(S) : Donald C. Young

It is certified that error appears in the above-identified patent and that said Letters Patent is hereby corrected as shown below:

Claim 1, column 27, line 17, after "ester" delete "," and insert -- and--; line 18, delete "epoxy and amino"; lines 21 and 22, delete "thiols when . . . thiolysis".

Add the following claims:

10. The method defined in claim 1 wherein said chalcogen comprises a member selected from the group consisting of oxygen, sulfur, and combinations thereof, and said molar ratio is within the range of about 1/2 to less than 2.

11. The method defined in claim 10 wherein said reactant comprises water and said reaction comprises hydrolysis.

12. The method defined in claim 1 wherein said reactant comprises an alcohol and said reaction comprises alcoholysis.

13. A method of hydrolyzing an organic compound having a chemical linkage selected from the group consisting of amido ester, acid ester and thioester linkages and combinations thereof, which comprises reacting said organic compound with water in the presence of a catalytically active amount of the monoadduct of sulfuric acid and a chalcogen-containing compound having the empirical formula

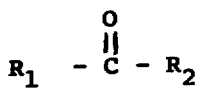

wherein each of $R_1$ and $R_2$ is independently selected from the group consisting of hydrogen, $NR_3R_4$ and $NR_5$, with at least one of the $R_1$ and $R_2$ being other than hydrogen, each of $R_3$ and $R_4$ is independently selected from the group consisting of hydrogen and monovalent organic radicals, and $R_5$ is a divalent organic radical.

UNITED STATES PATENT AND TRADEMARK OFFICE
CERTIFICATE OF CORRECTION

PATENT NO. : 4,942,254

DATED : July 17, 1990

INVENTOR(S) : Donald C. Young

It is certified that error appears in the above-identified patent and that said Letters Patent is hereby corrected as shown below:

14. The method defined in claim 13 wherein said reaction is conducted in the presence of a member selected from the group consisting of surfactants, polar solvents other than water, and combinations thereof.

15. The method defined in claim 13 wherein at least one of $R_1$ and $R_2$ is $NR_3NR_4$.

16. The method defined in claim 13 wherein said chalcogen-containing compound is selected from the group consisting of urea, thiourea, formamide and combinations thereof.

17. The method defined in claim 13 wherein said chalcogen-containing compound comprises urea.

Signed and Sealed this

Eleventh Day of February, 1992

*Attest:*

HARRY F. MANBECK, JR.

*Attesting Officer*     *Commissioner of Patents and Trademarks*